United States Patent [19]

Müller

[11] 4,427,889

[45] Jan. 24, 1984

[54] METHOD AND APPARATUS FOR MOLECULAR SPECTROSCOPY, PARTICULARLY FOR THE DETERMINATION OF PRODUCTS OF METABOLISM

[75] Inventor: Gerhard J. Müller, Aalen, Fed. Rep. of Germany

[73] Assignee: Carl Zeiss Stiftung, Oberkochen Wierttemberg, Fed. Rep. of Germany

[21] Appl. No.: 253,926

[22] PCT Filed: Aug. 12, 1980

[86] PCT No.: PCT/DE80/00119

§ 371 Date: Apr. 23, 1981

§ 102(e) Date: Apr. 17, 1981

[87] PCT Pub. No.: WO81/00622

PCT Pub. Date: Mar. 5, 1981

[30] Foreign Application Priority Data

Aug. 23, 1979 [DE] Fed. Rep. of Germany ....... 2934190

[51] Int. Cl.³ .............................................. G01J 1/00
[52] U.S. Cl. .................................... 250/339; 128/633
[58] Field of Search ............... 250/338, 339, 341, 343, 250/349; 356/39, 51, 432, 433; 128/633, 664

[56] References Cited

U.S. PATENT DOCUMENTS

| 3,405,268 | 10/1968 | Brunton | 356/51 |
| 3,459,951 | 8/1969 | Howarth et al. | 250/226 |
| 3,638,640 | 2/1972 | Shaw | 128/633 |
| 3,675,019 | 7/1972 | Hill et al. | 250/339 |
| 3,958,560 | 5/1976 | March | 128/633 |
| 4,044,257 | 8/1977 | Kreuzer | 250/344 |
| 4,100,416 | 7/1978 | Hirschfeld | 356/39 |
| 4,268,751 | 5/1981 | Fritzlen et al. | 250/343 |

FOREIGN PATENT DOCUMENTS 2724543 5/1977 Fed. Rep. of Germany ...... 128/633

Primary Examiner—Janice A. Howell

[57] ABSTRACT

Method and apparatus for molecular spectroscopy, particularly for the determination of products of metabolism.

The absorption of infrared radiation by a specimen (2) which contains the substance to be determined is measured. The absorption is measured simultaneously at two different wavelengths ($\lambda_1$, $\lambda_2$), the first wavelength ($\lambda_1$) being so selected that upon changes in concentration of the substance to be determined in the specimen (2) only a negligibly small change, if any, of the radiation absorption takes place, while the second wavelength ($\lambda_2$) lies in the region of a substance-specific absorption band of the substance to be determined. After measurement of the radiation intensities ($I_1$ and $I_2$) at the two wavelengths ($\lambda_1$, $\lambda_2$) the signal is standardized by formation of the quotient ($I_2/I_1$).

The method makes it possible to effect a quantitative reproducible measurement in the natural biological medium or in dialysates without pretreatment of the specimen and with only small amounts of substance. By suitable selection of the second wavelength ($\lambda_2$) a plurality of substances can be determined.

13 Claims, 12 Drawing Figures

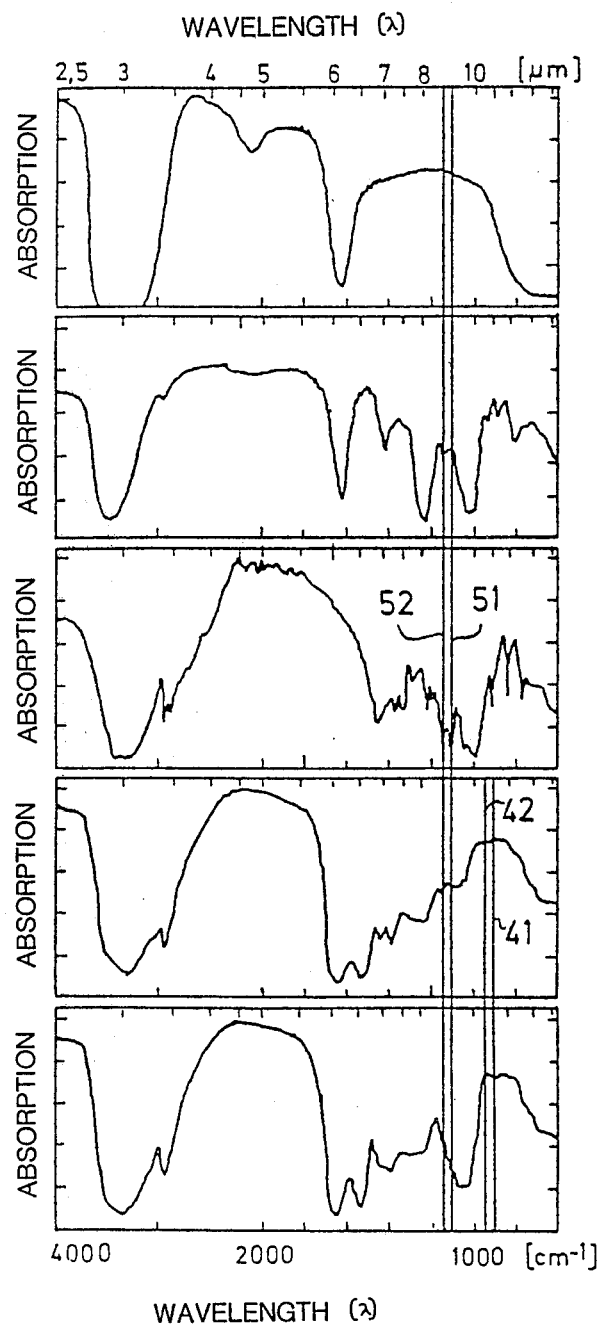

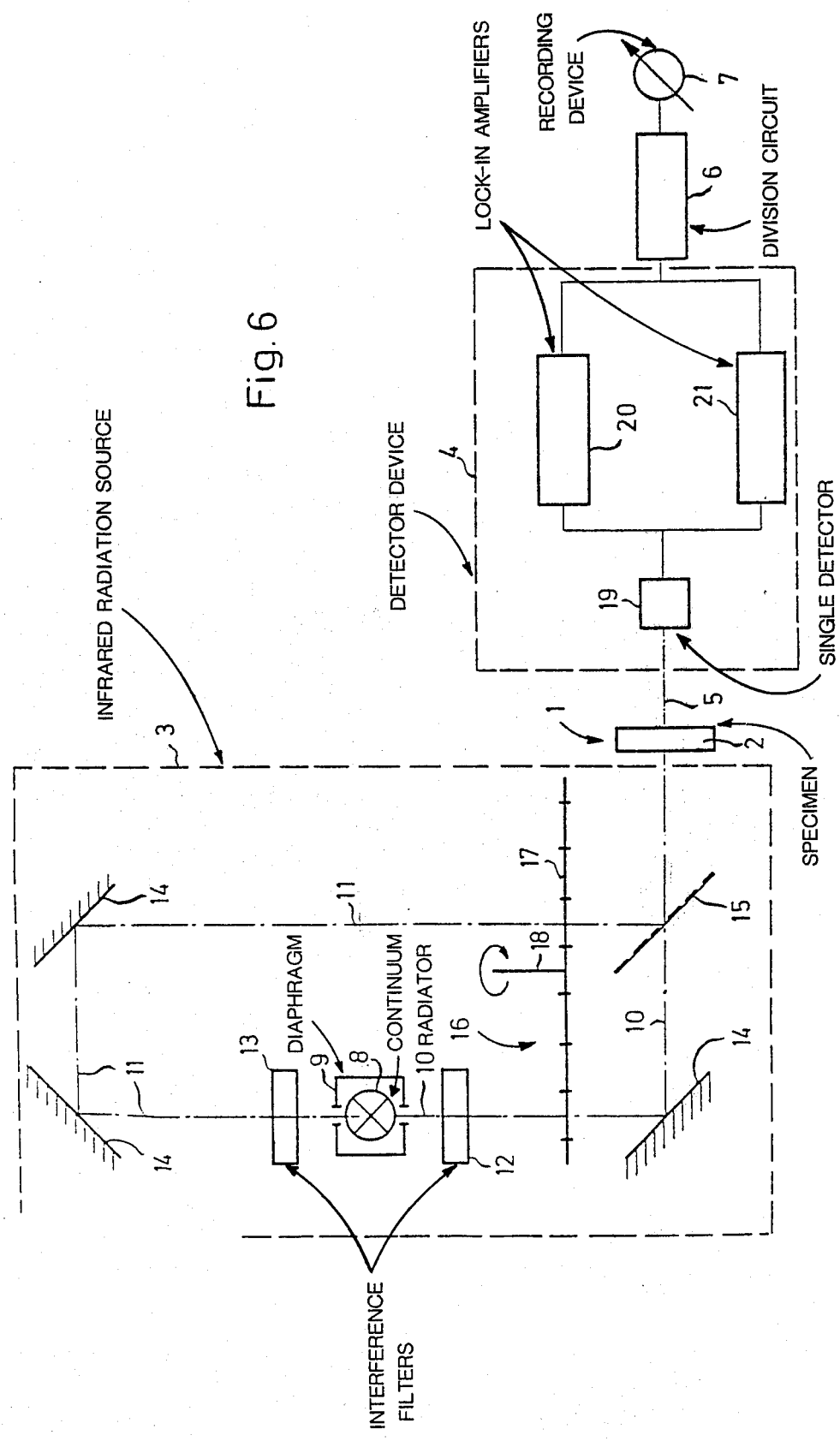

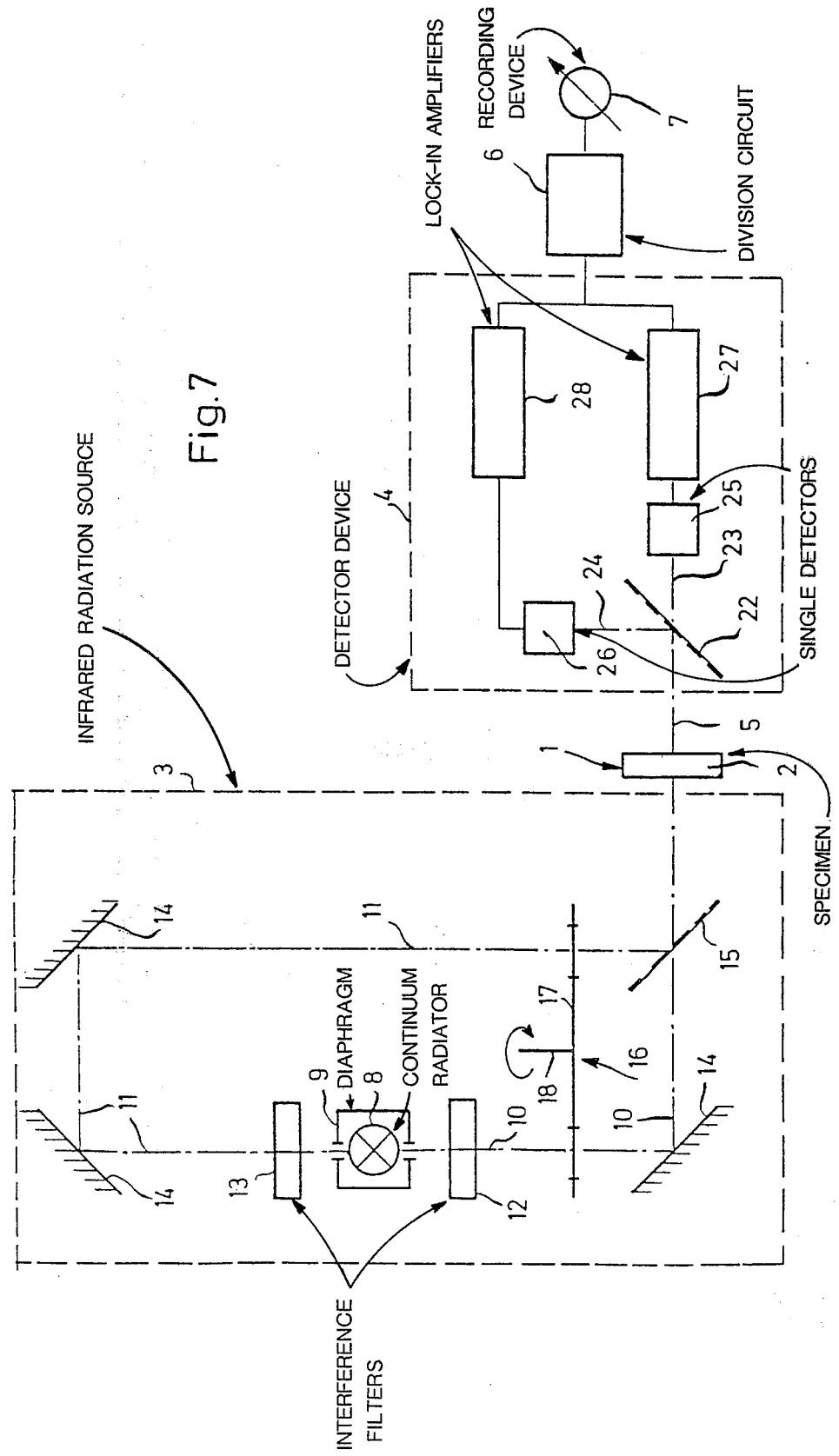

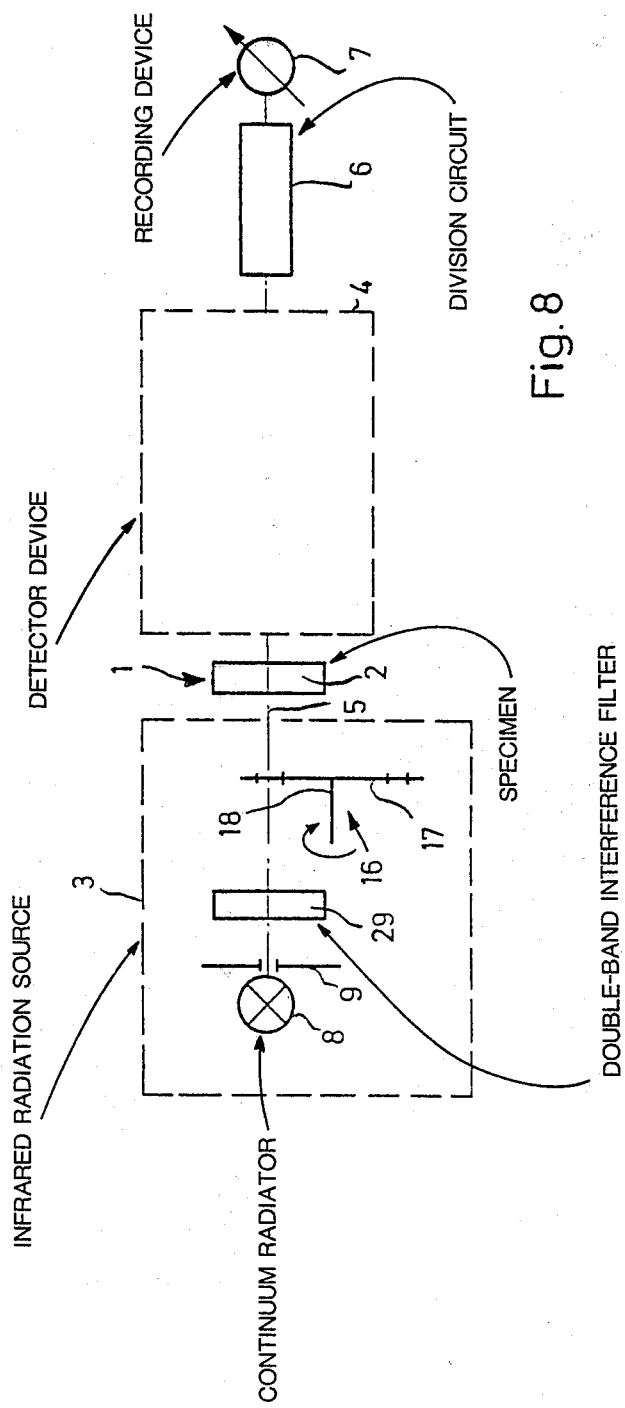

METHOD AND APPARATUS FOR MOLECULAR SPECTROSCOPY, PARTICULARLY FOR THE DETERMINATION OF PRODUCTS OF METABOLISM

The present invention relates to a method of molecular spectroscopy, particularly for the determination of products of metabolism, in which the absorption of infrared radiation by a specimen containing a substance to be determined is measured, as well as to an apparatus for the carrying out of this method.

The method and the apparatus of the invention can be used in particular for the determination of glucose in serum or in urine. Such a determination is of great importance for the recognition of diabetes mellitus and as check-up on the treatment thereof. The known determination by means of test strips in urine serves primarily to detect the disease. Although a well-stabilized diabetic can, in case of regular examination of the urine, get along with a few spot checks of blood glucose, the determination of the concentration of glucose in the blood is essentially of importance for treatment, verification of treatment and adjustment of the daily profile.

The known methods for the determination of glucose can be divided into three groups, namely biochemical, electrochemical and spectroscopic methods. Of these methods, the biochemical methods are suitable only as laboratory procedures; the electrochemical methods, to be sure, at present afford the most promising prospects for the development of implantable glucose sensors but are inferior in their precision and specificity to the spectroscopic methods, as the biochemical methods also are.

The biochemical and electrochemical methods furthermore have the common disadvantage that the specimen to be measured must be so prepared by addition of chemicals before the actual measurement process as to form reaction products which can be detected in the measurement. Thus continuous measurements are not possible.

In contradistinction to the biochemical and electrochemical methods, the glucose molecule is not modified in the spectroscopic method.

In addition, there are still a few non-specific methods which are practically no longer used. Thus, for instance, from German Pat. No. 2 724 543 a method is known for determining glucose based on the long-known polarimetry, which, however, is today rarely used because of insufficient specificity, it being suitable at most under favorable conditions for the determination of sugar in the urine.

A first possibility of determining products of metabolism by spectroscopic measurement is represented by laser Raman spectroscopy. The frequency of the exciter radiation is here in the visible spectral range. For the measurement, the portion in the spectrum of the scattered light which is shifted towards the red is used.

In measurements in whole blood the difficulty is encountered in this method of measurement that, due to the hemoglobin and the other chromophoric substances, blood exhibits strong absorption throughout the entire visible spectral range, which, to be sure, leads to a reinforcement of the resonance of the Raman scattering for these molecules but has a high fluorescence background associated with it and thus makes the detection of non resonance-reinforced bands difficult if not entirely impossible. This problem, to be sure, can be solved with the presently available possibilities of exciting the Raman scattering with short laser pulses in the subnanosecond range; however, the technical expenditure is so substantial that it will not be possible in the foreseeable future to find any practical method with it for samples of whole blood.

Another possibility of avoiding the disturbance by fluorescence of the chromophores consists in operating in the infrared spectral range, i.e. in recording directly the infrared spectrum of the specimen. However, since the preparation of the specimen as well as the recording and evaluation of the spectrum are time-consuming and complicated, infrared spectroscopy of the type customary up to now does not constitute competition for the other methods which exist.

Another spectroscopic method is the so-called attenuated total reflectance (ATR) spectroscopy, i.e. total reflectance spectroscopy with transversely attenuated wave.

Thus it is known, for instance, from West German Application for Patent No. 2 606 991 to use a $CO_2$ laser in combination with the well-known ATR spectroscopy to determine glucose or else other products of metabolism. This can be done, however, only in pure solutions; in multi-component systems or even in whole blood this method necessarily fails, due to basic difficulties.

Thus, for instance, the Lambert-Beer law for ATR spectroscopy applies only for an absorption coefficient within the range of 0.1 and less and for an angle of incidence of approximately 60° or more, referred to the materials customary in IR, and furthermore only in case of sufficiently large wave lengths, and even then only approximately for isotropic specimens. Even upon in-vitro measurements in whole blood therefore difficulties would already arise caused, for instance, also by the protein adsorption on the reflection surfaces, which convert the system into anisotropy.

In spectroscopic measurements in the infrared spectral region, the absorption contribution of the solvent or embedment material for the substance to be determined is customarily compensated for by the use of a reference ray in addition to the actual measurement ray, infrared radiation of the same wavelength being used in both rays. The required reproducibility of the measurement in the reference ray, however, requires pretreatment of the specimen and is not directly applicable to substances to be examined which are present in the natural biological milieu.

The object of the present invention is now to provide a method for determining products of metabolism which makes possible quantitative reproducible measurement in the natural biological milieu without pretreatment of the specimen and therefore also without consumption of chemicals, and in addition requires only small amounts of substance.

Proceeding from the basis of the method described in the preamble to claim 1, this object is achieved in the manner that measurement is effected simultaneously at two different wavelengths of the infrared radiation, the first wavelength being selected in such a manner that upon changes in concentration of the substance to be determined in the specimen no change in the infrared absorption or only a negligible change occurs, while the second wavelength is so selected that it lies in the region of a substance-specific absorption band of the substance to be determined and that the quotient of the absorption values measured at these two wavelengths is formed.

The method of the invention can therefore be characterized as a two-wavelength method in which the first wavelength lies in a "quasi-isosbestic" range while the other wavelength lies in the range of a substance-specific absorption band, in such a manner that in the case of this latter wavelength a change in absorption is caused only by a change in concentration of the substance examined. In general, wavelengths of these properties can be readily selected on basis of existing infrared absorption spectra of the specimens in question since in addition to the substance-specific absorption bands there are quasi-isosbestic ranges also in multi-component mixtures.

By means of the method of the invention it is possible, for instance, to determine glucose in human whole blood rapidly and dependably. It is also possible to measure other products of metabolism such as, for instance, ethyl alcohol, urea, uric acid, creatinine, peptide decomposition products, polystyrol and lipids in the blood or in other body liquids. The measurement can also be effected in dialysates, i.e. in liquids which are not body fluids but contain metabolism products. One such dialysate is, for instance, the liquid used for dialysis in kidney patients.

The method of the invention can be carried out by determining the absorptions at the two different wavelengths by means of transmission spectroscopy or by means of reflectance spectroscopy, and particularly ATR spectroscopy. Transmission measurements have the advantage over measurements by means of ATR spectroscopy, for instance in the case of the determination of glucose in whole blood, that the Lambert-Beer law applies here and that they can be calibrated by biochemical absolute-determination for the obtaining of quantitative measurement values.

The sample to be measured is advisedly present in the form of a smear or film on a disposable or throw-away specimen support of plastic. The support material is so selected that it has only a slight absorption of its own in the region of the first and second wavelengths. The specimen support can be developed as a flat microscope slide, but also possibly as a flow-through or trough cell.

As already mentioned, there are also quasi-isosbestic regions in multi-component mixtures so that a wavelength can be found for which even upon changes in concentration of several substances in the specimen no change in the infrared radiation absorption takes place or only a negligibly small change. In this way, several substances in the specimen can be determined one after the other in one and the same apparatus by changing the first wavelength in such a manner that it lies in each case within the region of a substance-specific absorption band. In each case the measurement signal is standardized, the specimen itself serving as reference.

An apparatus for the carrying out of the method of the invention is characterized by a source of infrared radiation for the production of an infrared radiation beam which consists of infrared radiation of at least a first and a second wavelength, the first wavelength being so selected that upon changes in concentration of the substance to be determined in the specimen no change in the infrared radiation absorption takes place or else only a negligibly small change while the other wavelength is so selected that it lies in the range of a substance-specific absorption band of the substance to be determined, by a detector device for the separate measurement of the absorption values of the infrared radiation of the different wavelengths, and by a division circuit arranged behind the detector device for forming the quotient of the absorption values ascertained.

The source of infrared radiation can contain a strong continuum radiator or one or more lasers, in which connection gas or solid lasers can be used. For the separating out of the two wavelengths used for the measurement interference filters can be provided or suitably developed beam splitters.

It is advantageous to use only one detector on the reception end and to make the radiation beams of different wavelength distinguishable by different modulation.

By the formation of the quotient of the absorption values which are measured for the two wavelengths one obtains a standardized measurement signal, the specimen itself serving as reference.

Further features of the invention are set forth in the subordinate claims.

The invention will be described in further detail below with reference to FIGS. 1 to 12 of the accompanying drawings, in which:

FIG. 1 is an infrared absorption spectrum of water;

FIG. 2 is an infrared absorption spectrum of heparin;

FIG. 3 is an infrared absorption spectrum of D-glucose;

FIG. 4 is an infrared absorption spectrum of dried human whole blood the glucose content of which is within the normal physiological range;

FIG. 5 is an infrared absorption spectrum of dried human whole blood which has been enriched with D-glucose to such an extent that the glucose content lies within the pathological range;

FIG. 6 shows a first embodiment of an apparatus in accordance with the invention;

FIG. 7 shows a second embodiment of an apparatus;

FIG. 8 shows a third embodiment of the invention with a modified source of infrared radiation;

Figure 9:
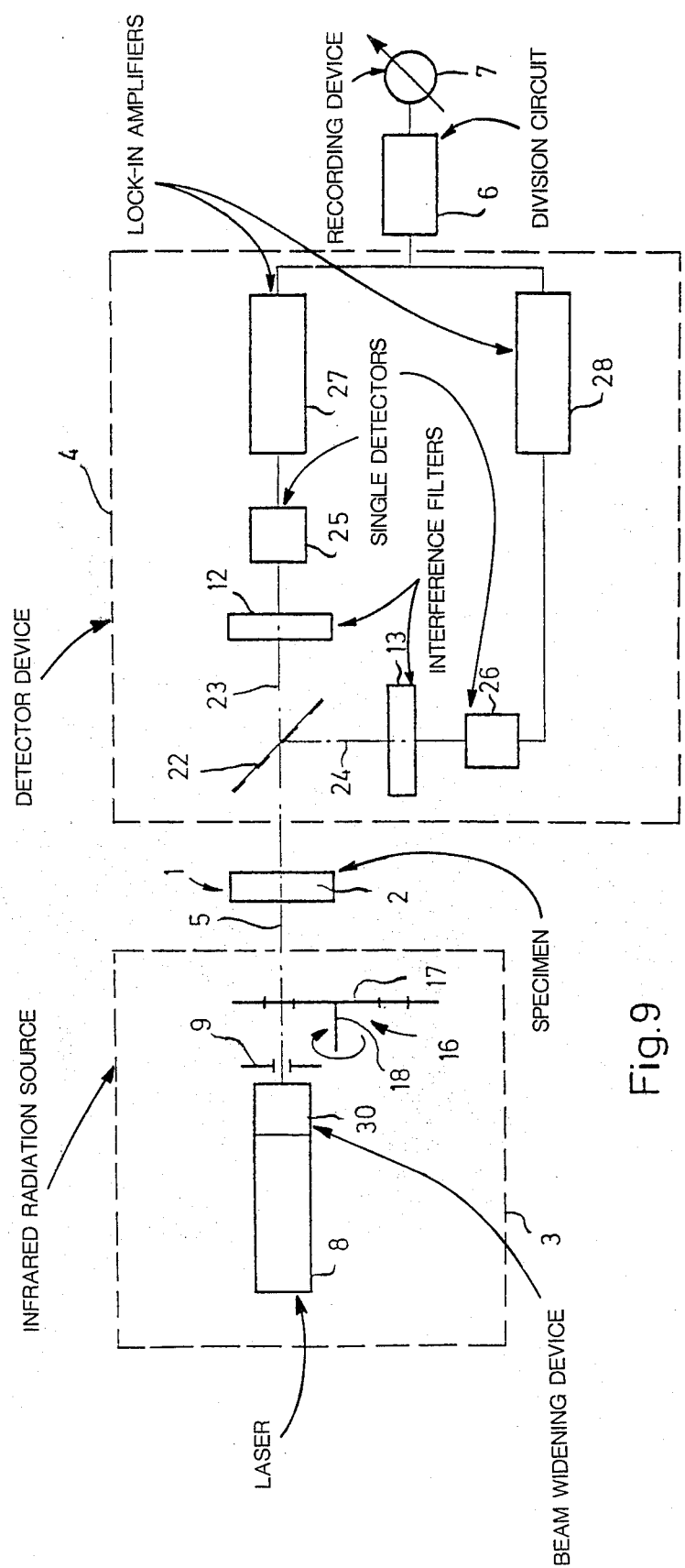
FIG. 9 shows a fourth embodiment of the invention.

The selection of the two wavelengths used for the measurement will be described in connection with FIGS. 1 to 5, using the determination of glucose as example. One essential difficulty in this determination in whole blood or urine is that body fluids consist of water to a high percentage. Water, however, has an absorption coefficient of 700 cm$^{-1}$ in the region of the glucose absorption in the infrared. Glucose, on the other hand, has an absorption coefficient of merely about 0.1 cm$^{-1}$ in this range. This difficulty, which is present in general in IR measurements in aqueous solutions, is customarily avoided by a so-called double-beam method. In it the absorption of the solvent or the embedment means is compensated for by a reference ray path in which a specimen which consists only of water is present. By the use of lasers instead of the conventional sources of light this problem can be reduced further.

The double-beam method, however, has the fundamental disadvantage that a complicated preparation of the specimen is necessary in order to make meaningful use of the reference ray path possible.

In the method of the invention, a double-wavelength method is used instead of the double-beam method. In it, the absorption of the specimen is determined simultaneously at two different wavelengths. The two wavelengths are so close to each other that dispersive effects can be kept small. This permits of measurement in the biological medium without complicated and tedious prior treatment of the specimen.

The first wavelength $\lambda_1$ is selected in such a manner that upon changes in concentration of the substance to be examined in the specimen only a negligibly small change of the absorption, if any, takes place, i.e. $\lambda_1$ should lie at the "isosbestic point" or in a "quasi-isosbestic" region.

Such a quasi-isosbestic region is indicated in FIGS. 4 and 5 by the lines 41 and 42. It can be seen that in this region upon a change of the glucose concentration there is only a negligibly small change in the absorption. This absorption, therefore, corresponds to the fundamental absorption of the specimen and is suitable for the standardization of the measurement signal.

The line 41 corresponds to the value 940 cm$^{-1}$ and the line 42 to the value 950 cm$^{-1}$.

The second wavelength $\lambda_2$ is selected in such a manner that it lies on a substance-specific absorption band. This condition is satisfied by wavelengths in the region between the two wavelengths designated 51 and 52 in FIGS. 1 to 5. Line 51 corresponds to a value $\lambda_2$ of 1090 cm$^{-1}$ and line 52 to 1095 cm$^{-1}$. From FIGS. 3 and 2 it can be seen that the region indicated lies on an absorption band of glucose and at the same time, however, in the region of minimal absorption for heparin. The mucopolysaccharide heparin is present in whole blood in a relatively high percentage in the basophilic leucocytes. In the normal case, the influence is not too high, about 0.5%, but in borderline pathological situations with increased number of leucocytes or else after administration of heparin as an anticoagulant a substantial disturbance of the glucose measurement can take place. By the selection of the wavelength $\lambda_2$ shown, disturbance of the measurement by heparin in the specimen is avoided.

If a $CO_2$ laser is used as source of radiation the $\lambda_2$ lines correspond to the laser lines R (40) to R(52) and the $\lambda_1$ wavelength range lies between the $CO_2$ laser lines P(14) to P(26). The wavelength selection is advisedly effected by suitable interference filters which can be produced in these regions in accordance with the prior art with a half width of about 5 cm$^{-1}$. Instead of a $CO_2$ laser there may also be used a semiconductor laser, for instance a $Pb_{1-x}-Sn_x-Te-$ or a Raman laser, or else a continuum irradiator with frequency selection. The detection of the measurement signal is effected with the methods and apparatus customary in the prior art.

The embodiments of devices for the determination of products of metabolism shown in FIGS. 6 to 10 can be used both for transmission spectroscopy and for ATR total reflect and spectroscopy with transversely attenuated infrared light waves. In this connection, the specimen carrier 1, which has been only schematically indicated, in or on which the specimen 2 is provided is made preferably either as microscope slide or as cell from, for instance, a copolymer of polyethylene and polypropylene, depending on whether the specimen 1 is irradiated vertically or horizontally.

Each of the embodiments shown has a source of infrared radiation 3 and a detector device 4. Within the infrared radiation beam 5 which forms the ray path between the source 3 and the detector 4 there is located the specimen carrier 1 bearing the specimen 2 to be measured.

The source of infrared radiation 3 is developed in such a manner that it produces the infrared radiation beam 5 which consists of infrared radiation of a first and a second wavelength $\lambda_1$ and $\lambda_2$ respectively. The detector device 4 is developed in such a manner that it measures separately the absorption or intensity values of the infrared radiation of the different wavelengths $\lambda_1$ and $\lambda_2$. Behind the detector device 4 there is provided a divider circuit 6 to which the two signals $I_1$ and $I_2$ determined by the detector device 4 are fed and which forms the quotient $Q=I_2/I_1$, in which $I_2$ is the absorption or intensity value corresponding to the wavelength $\lambda_2$ while $I_1$ is the absorption or intensity value corresponding to the wavelength $\lambda_1$. Behind this divider circuit 6 there is an indicating and/or recording device 7 which can be developed, for instance, as recorder, printer or digital or analog display instrument or the like.

In the embodiment shown in FIG. 6, the infrared radiation source 3 has a strong continuum radiator 8 such as, for instance, a Globor or Nernst rod. By means of a diaphragm 9 a first and a second infrared radiation beam 10 and 11 respectively are stopped out. For the selecting of the two wavelengths $\lambda_1$ and $\lambda_2$ from the continuum spectrum of the source of radiation 8 a first interference filter 12 is arranged in the ray path of the individual ray 10, it passing essentially only radiation of the wavelength $\lambda_1$, while in the ray path of the second individual ray 11 there is arranged a second interference filter 13 which passes substantially only radiation of the wavelength $\lambda_2$.

Figure 11:
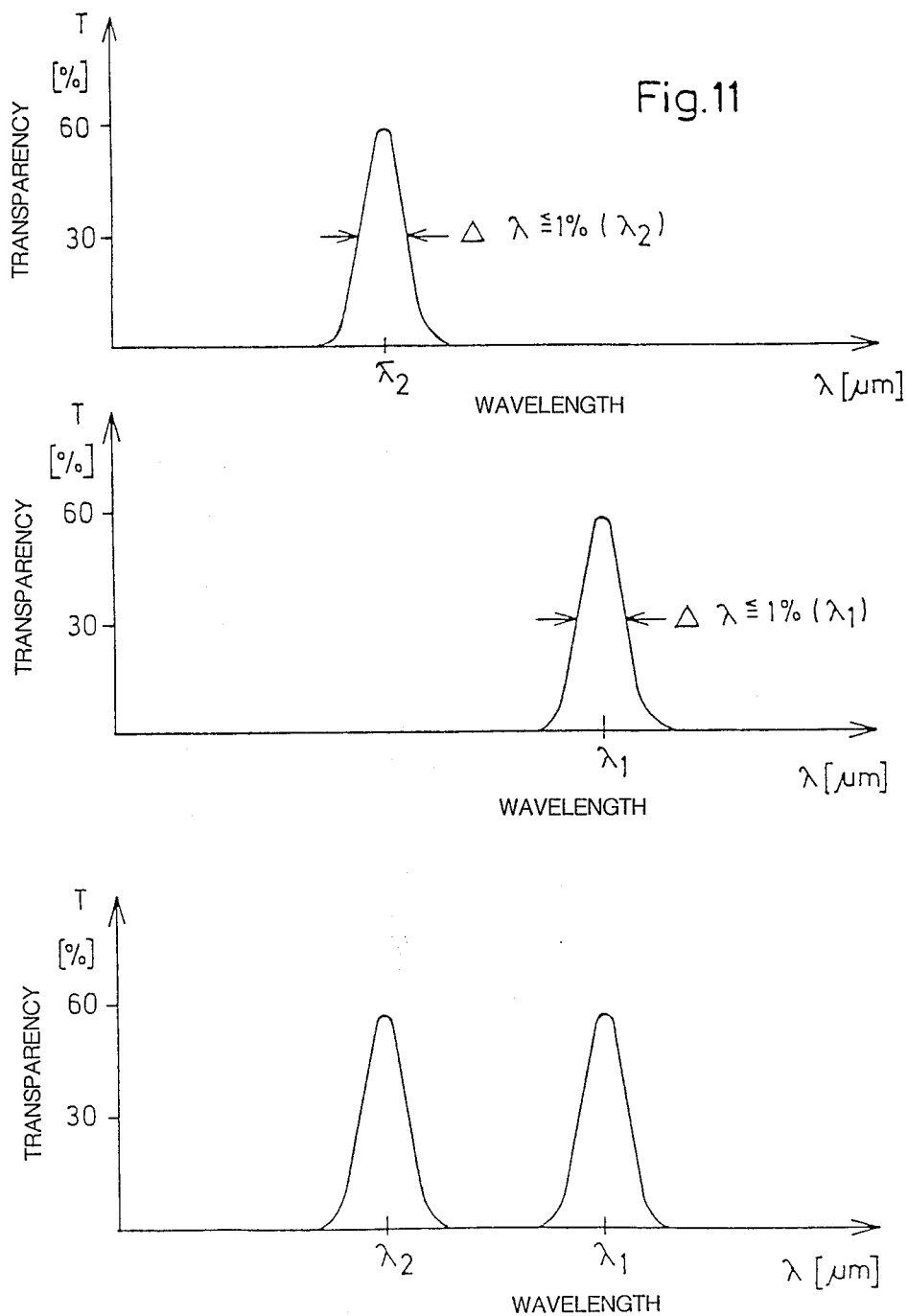
FIG. 11 shows transmission curves of two single-band interference filters such as used in the embodiments of FIGS. 6, 7 and 9; and a transmission curve of a double-band interference filter such as used in FIG. 8.

The basic course of the transmission function of the interference filters 12, 13 is shown in the upper and middle parts of FIG. 11 in which the transparency T in percent is plotted over the wavelength $\lambda$ in $\mu$m. The half-width value $\Delta\lambda$ should be smaller than or equal to 1% of the corresponding wavelength $\lambda_1$ or $\lambda_2$ which is to be transmitted.

The two individual rays 10, 11 are combined by mirrors 14 and a wave-length selective beam divider 15 to form a single infrared radiation beam 5 after they have previously been modulated by a chopper 16 with different frequencies $f_1$ (modulation frequency of the infrared radiation beam 10) and $f_2$ (modulation frequency of the infrared radiation beam 11) respectively. The fact that different frequencies result is indicated in the manner that the chopper disk 17 of the chopper 16 cuts the infrared radiation beam 11 at a place located closer to the axis of rotation 18 of the chopper 16 than the infrared radiation beam 10, and the chopper blade for the two beams (10, 11) has a different number of segments.

Figure 12:
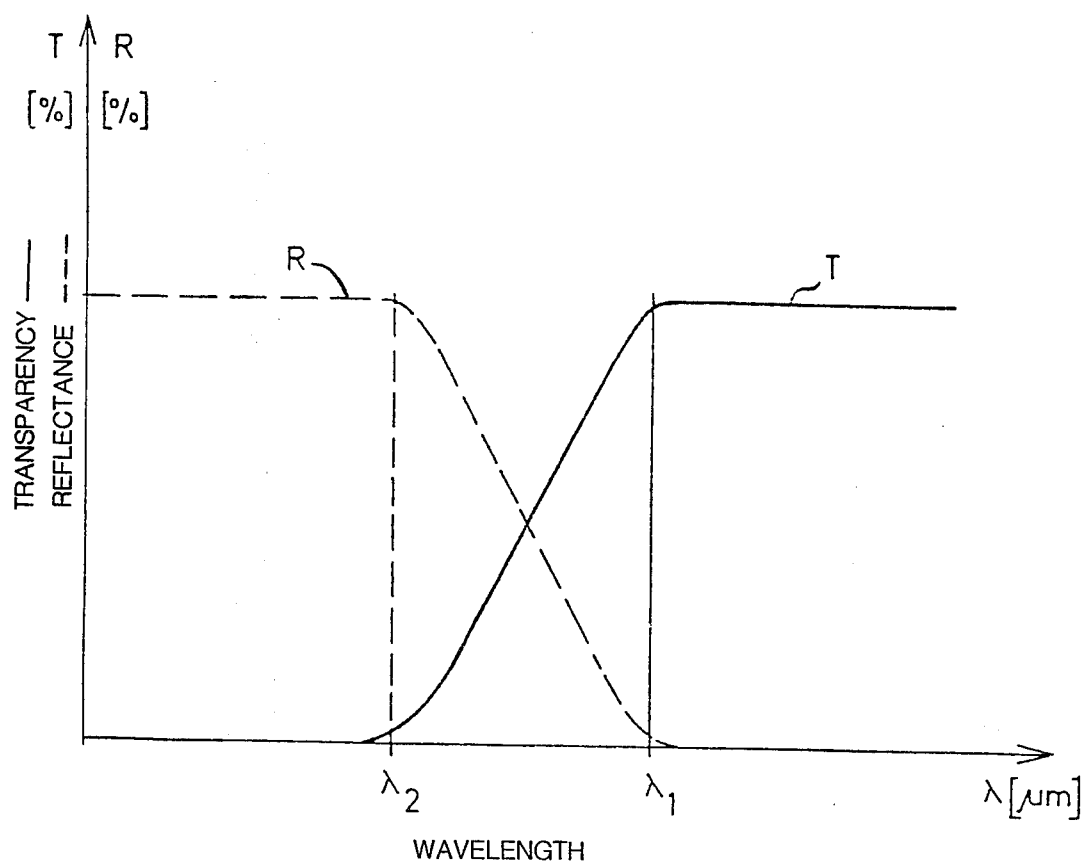
FIG. 12 shows the transmission curves of a wavelength-selective beam splitter such as provided in the embodiments of FIGS. 7 and 9.

The transmission function of the wavelength-selective beam splitter 15 is shown in FIG. 12 in which the transparency T and the reflectivity R are plotted, in each case in percent, over the wavelength in $\mu$m, and the wavelengths $\lambda_1$ and $\lambda_2$ entered.

The radiation beam 5 passes through the specimen 2, which may for instance be a smear of a drop of blood, on a specimen holder 1 developed as a microscope slide. This slide may consist, for instance, of a copolymer of polyethylene and polypropylene. After passage through the specimen 2, the infrared radiation beam 5 passes into the detector device 4 and comes here against a single detector 19 which has practically the same sensitivity in the range in which the wavelengths $\lambda_1$ and $\lambda_2$ are. For example, the detector 19 can be a pyroelectric receiver, such as for instance a triglycin-sulfate crystal, referred to in abbreviated fashion also as TGS crystal. This practically identical sensitivity is necessary in order that the following electronic system can be operated with the same time constants. The output signal of the detector 19 is fed to two parallel lock-in amplifiers 20, 21 (phase-sensitive rectifiers with possibly amplifier behind same), one of which is tuned to the modulation frequency $f_1$ of the infrared radiation portion of the wavelength $\lambda_1$ and the other to the modulation frequency $f_2$ of the infrared radiation portion of the wavelength $\lambda_2$. At the output of the lock-in amplifier 20 the abovementioned intensity value $I_1$ or a signal proportional to it is obtained, while at the output of the lock-in amplifier 21 there is available the above-indicated intensity value $I_2$ or a signal proportional to it. These two signals are fed into the following division circuit 6 which produces therefrom the standardized concentration-proportional signal $Q = I_2/I_1$.

In the embodiment shown in FIG. 7, the chopper 16 is so arranged and developed that it modulates two individual rays 10 and 11 with the same chopping frequency f. Accordingly a second wavelength-selective beam splitter 22 is provided in the corresponding detector device 4 and it divides the sole infrared beam 5 impinging upon it into a first individual beam 23 of the wavelength $\lambda_1$ and a second individual beam 24 of the wavelength $\lambda_2$. The first individual beam 23 comes onto a detector 25 and the second individual beam 24 strikes a second detector 26. These detectors 25, 26 may be of the same type as the detector 19 of FIG. 6.

The lock-in amplifiers 27 and 28 arranged behind the two detectors 25, 26 respectively, both of which amplifiers are tuned to the modulation frequency f, in their turn produce at their outputs intensity values $I_1$ and $I_2$ respectively from which the above-indicated quotient Q is formed in the division circuit 6.

FIG. 8 shows an embodiment in which only a single radiation beam, namely the infrared radiation beam 5, is stopped-out by the diaphragm 9 from the radiation of the source of radiation 8, which is also developed as continuum radiator. This beam passes through a double-band interference filter 29 and the chopper disk 17 of a chopper 16 and then passes through the specimen 2. The transmission curve of this double-band interference filter 29 is shown in the lower part of FIG. 11 and, as can be noted from a comparison with the middle and upper parts of FIG. 11, represents a combination of the transmission curves of the two interference filters 12 and 13 which are used in the embodiments of FIGS. 6 and 7.

The detector device 4 in FIG. 8 can be developed in the manner shown in FIG. 7.

FIG. 9 shows an embodiment in which the infrared radiation source 3 has as source of light a laser 8, for instance a $CO_2$ laser or a Raman laser with multi-line emission. This laser is provided with a beam-widening device 30. By means of the diaphragm 9 a single radiation beam, namely the infrared radiation beam 5 is stopped-out and is modulated before it passes through the specimen 2, by means of a chopper 16 with a chopping frequency f.

The detector device 4 is essentially of the same construction as shown in FIG. 7; however, for purposes of wavelength selection a first interference filter 12 is arranged in the ray path of the first individual beam 23 between the wavelength-selective beam splitter 22 and the first detector 25 so that the latter receives only infrared radiation of the wavelength $\lambda_1$ while a second interference filter 13 which passes only radiation of the wavelength $\lambda_2$ is provided in the ray path of the second individual beam 24 between the wavelength selective beam splitter 23 and the second infrared radiation detector 26.

The embodiment of FIG. 9 can also be modified in such a manner that by the splitting up and recombination of the radiation beam emerging from the beam widening device 30, with selection of the wavelengths $\lambda_1$ and $\lambda_2$ and of a double-frequency modulation by means of a chopper 16 in accordance with the embodiment of FIG. 6, it is possible to use a detector device 4 of the type shown in FIG. 6 which requires only a single detector 19.

Figure 10:
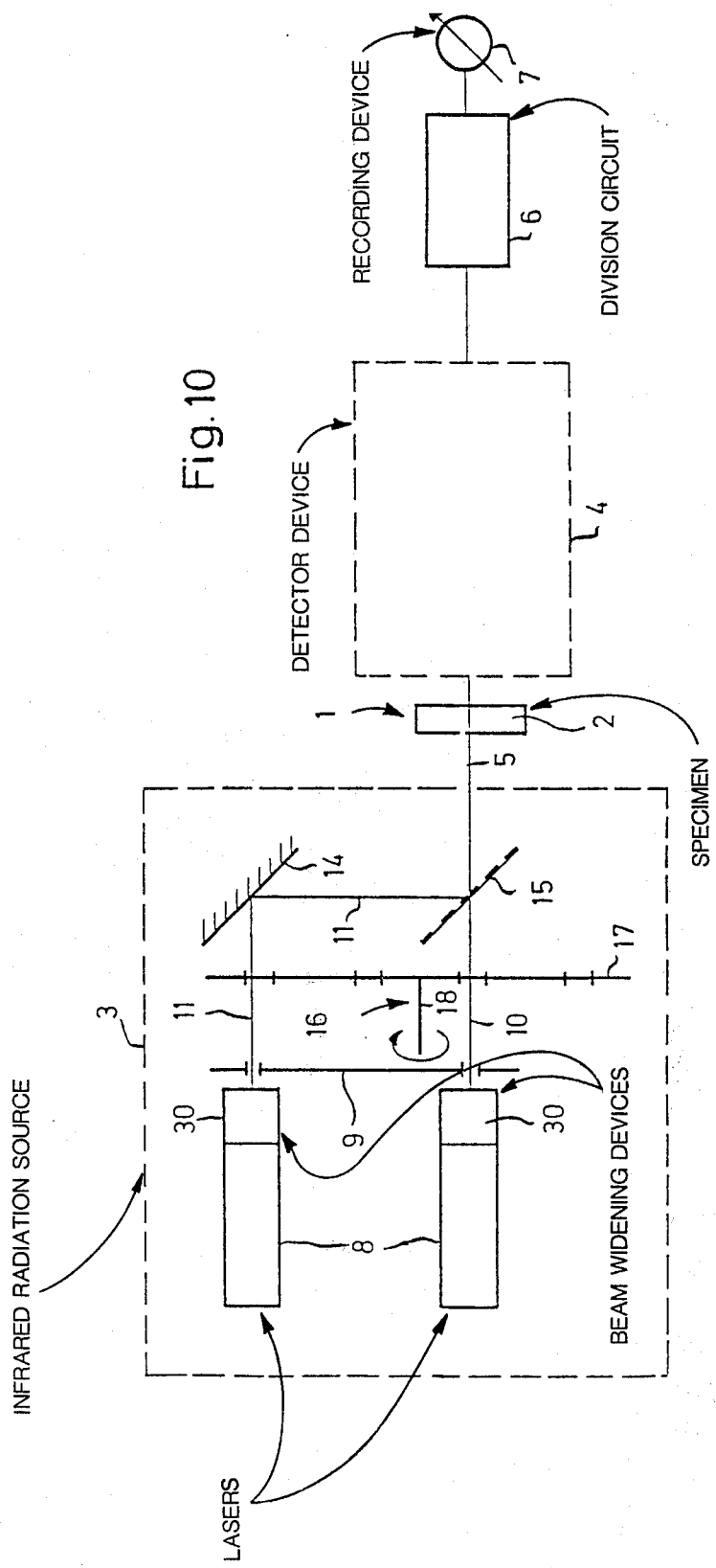
FIG. 10 shows a fifth embodiment of the invention.

In FIG. 10 there is shown an embodiment in which two monochromatic lasers 8 are provided, one of which has the emission wavelength $\lambda_1$ and the other the emission wavelength $\lambda_2$. These lasers 8 can, for instance, be $Pb_{1-x}Sn_xTe$ lasers so that, after passage of the laser radiations through the beam-widening device 30, a first individual beam 10 is produced by the diaphragm 9, which beam contains only infrared radiation of the wavelength $\lambda_1$, as well as a second individual beam 11 which contains only infrared radiation of the wavelength $\lambda_2$. These two individual beams are modulated in a manner similar to that described in FIG. 6 with two different chopping frequencies $f_1$ and $f_2$ respectively and are combined to form a common infrared radiation beam 5 by a mirror 14 and a wavelength-selective beam splitter 15. The detector device 4 can in this embodiment be of the type shown in FIG. 6 but it can also be developed in the manner shown in FIG. 7 provided that the two individual beams 10, 11 in FIG. 10 are modulated with the same chopping frequency f.

The specimen space can also be developed as a flow-through cell of small layer thickness. This is particularly of interest when the method is to be used for continuous measurement, for instance upon dialysis with an artificial kidney. In this case of use what is of interest is less the glucose determination than rather the determination of peptide fission products, defect hormones, urea, uric acid and creatinine in the dialysate. The isosbestic or quasi-isosbestic region for $\lambda_1$ is in this connection substantially the same as in the glucose measurement but the second wavelength $\lambda_2$ must be selected in each case in accordance with the substances. The optical and electrical construction of the evaluation apparatus itself is selected in accordance with one of the embodiments shown.

It is also possible to determine several substances simultaneously with the method of the present invention. In that case more than two wavelengths must then be radiated simultaneously through the specimen, one of these wavelengths lying in an at least quasi-isosbestic region and the others being selected in each case adapted to the substances to be investigated. Thus it is readily possible, for instance, to determine glucose, ethyl alcohol, uric acid and creatinine simultaneously with the use of five different wavelengths. The standardization is effected in each case by the fifth wavelength, which lies in a quasi-isosbestic range, for instance in the range shown in FIGS. 1 to 5.

I claim:

1. A method for the spectroscopic determination of glucose concentration in an unpretreated multi-component specimen selected from the group of whole blood and urine which comprises the steps of:

(a) simultaneously measuring the absorption values of infrared radiation by said specimen at a first wavelength lying within the infrared spectral range of 940 to 950 cm$^{-1}$ and a second wavelength lying within the infrared spectral range of 1090 to 1095 cm$^{-1}$; and (b) standardizing the measurement by forming the quotient of the absorption values of the first and second wavelengths:

whereby the glucose concentration is proportional to the absorption value measured at second wavelength, and the absorption value measured at said first wavelength is essentially independent of said concentration.

2. A method according to claim 1, wherein the absorption value of said first and second wavelengths is determined by means of transmission spectroscopy.

3. A method according to claim 1, wherein the absorption value of said first and second wavelengths is determined by means of reflection spectroscopy.

4. A method according to claims 2 or 3, wherein the specimen is provided as a smear or film.

5. A method according to claims 2 or 3, wherein the infrared radiation of the first and second wavelengths are modulated at different frequencies.

6. An apparatus for determining the concentration of glucose in an unpretreated multi-component specimen selected from the group of whole blood and urine, comprising means for generating a radiation beam, said beam comprising a first wavelength lying within the infrared spectral range of 940 to 950 cm$^{-1}$ and a second wavelength lying within the infrared spectral range of 1090 to 1095 cm$^{-1}$; means for positioning the specimen in said radiation beam; a detector means for the separate but simultaneous measurement of the absorption values of the infrared radiation at said first and second wavelengths: and a division circuit adapted to form the quotient of the absorption values of said first and second wavelength.

7. An apparatus according to claim 6, wherein the means for generating said radiation beam comprising said first and second wavelengths includes a source of infrared radiation; a diaphragm for stopping-out first and second individual radiation beams; a first interference filter positioned within the path of the first individual radiation beam, said first interference filter being adapted to pass only infrared radiation of said first wavelength; a second interference filter positioned within the path of the second individual radiation beam, said second interference filter being adapted to pass only infrared radiation of said second wavelength; and means for deflecting and combining said first and second individual beams into said single beam comprising said first and second wavelength prior to passing through said specimen.

8. An apparatus according to claim 7, which further includes a chopper positioned within the ray path of the first and second individual radiation beams adapted to modulate the first individual ray beam with a first frequency and to modulate the second individual radiation beam with a second frequency.

9. An apparatus according to claim 8, wherein the detector means includes a single infrared radiation detector the output of which is fed into first and second parallel lock-in amplifiers said first amplifier being tuned to the first frequency and said second amplifier being tuned to the second frequency, and the outputs of the lock-in amplifiers being connected to the division circuit.

10. An apparatus according to claim 6, wherein said means for positioning said specimen is a disposable specimen support constructed of a plastic which has only a slight absorption of its own within the range of the first and second wavelengths.

11. An apparatus according to claim 6, wherein a strong continuum radiator is provided to generate said infrared radiation.

12. An apparatus according to claim 6, wherein one or more lasers are provided to generate said infrared radiation.

13. An apparatus according to claim 6, wherein the means for generating said radiation beam comprising said first and second wavelengths includes a source of infrared radiation; a diaphragm for stopping-out a single infrared radiation beam; and a double-band interference filter which passes only infrared radiation of said first and second wavelengths.

* * * * *